(12) United States Patent
Liem et al.

(10) Patent No.: US 6,308,555 B1
(45) Date of Patent: Oct. 30, 2001

(54) ROTATIONAL SHOCK TESTER APPARATUS

(75) Inventors: Andre Y. Liem; Joseph C. Liu; ChoonKiat Lim; Sen Chai Khew, all of Singapore (SG)

(73) Assignee: Seagate Technology LLC, Scotts Valley, CA (US)

( * ) Notice: Subject to any disclaimer, the term of this patent is extended or adjusted under 35 U.S.C. 154(b) by 0 days.

(21) Appl. No.: 09/306,149

(22) Filed: May 6, 1999

Related U.S. Application Data

(60) Provisional application No. 60/084,662, filed on May 7, 1998.

(51) Int. Cl.$^7$ .................................................. G01N 19/02
(52) U.S. Cl. ..................... 73/12.06; 73/12.01; 73/12.07; 73/12.09; 73/12.12
(58) Field of Search ................................ 73/12.01, 12.04, 73/12.06, 12.07, 12.09, 12.12, 12.13, 12.14

(56) References Cited

U.S. PATENT DOCUMENTS 6,050,127 * 4/2000 Rao et al. ................................ 12/13

* cited by examiner

*Primary Examiner*—Hezron Williams
*Assistant Examiner*—Maurice Stevens
(74) *Attorney, Agent, or Firm*—Merchant & Gould P.C.

(57) ABSTRACT

Embodiments of apparatus are directed to a rotational shock tester system comprising a disc drive support system, a drop mechanism and an impact apparatus. The disc drive support system includes a rotation plate, wherein a disc drive is coupled to the rotation plate. The drop mechanism is coupled to the disc drive support system and includes an elevating apparatus, wherein the elevating apparatus elevates and releases the rotation plate which is supporting the disc drive. The impact apparatus is releasably coupled to the drop mechanism and is aligned with the rotation plate such that upon release of the rotation plate, the rotation plate impacts the impact apparatus such that the impact apparatus imparts an angular acceleration to the rotation plate and imparts a rotational shock to the disc drive.

6 Claims, 3 Drawing Sheets

ROTATIONAL SHOCK TESTER APPARATUS

RELATED APPLICATIONS

This application claims the benefit of provisional patent application Ser. No. 60/084,662, filed May 7, 1998.

FIELD OF THE INVENTION

This invention is directed to a rotational shock tester apparatus; more specifically, to an apparatus for measuring rotational shock tolerances of a latch for an actuator for use in a disc drive system.

BACKGROUND OF THE INVENTION

The ability to shock test disc drives allows disc drive manufacturers to improve the design of their disc drive systems, which, in most instances, improves the performance and stability of the disc drive during use and transport. Previously, only linear shock test systems existed.

Although the linear shock testers allowed the measurement of the amount of force required to break the disc drive, these testers nonetheless did not measure rotational shock tolerances of the disc drive elements. The amount of force imparted from a rotational shock that a disc drive, such as, for example, a hard disc drive ("HDD"), can withstand provides an indication as to the amount of force required to uncouple a latch mechanism of an actuator such that the actuator is displaced, or unparked, from its parking zone. If the actuator is displaced from the parking zone, the head, which is disposed at one end of the actuator, will adhere to the media in the data zone. The adherence of the head to the media is called stiction. If stiction occurs, the drive cannot be started again.

In an attempt to determine the amount of force imparted from rotational shock that a disc drive can sustain, rotational shock testers have been designed. In current designs, such as, for example, the designs by GHI Systems, the rotational shock tester induces rotational acceleration by a spring-latch, similar to a catapult. At least one problem with this design is that the center of rotation may not be coincide the desirable location on the test specimen, such as, for example, the spindle, the center of the pivot of the actuator arm or any location allowing the test specimen to be off-set.

Although the rotational shock testers allow for the measurement of rotational information, currently used shock testers are stand-alone testing systems and do not provide any information that allows an evaluation of the design of the disc drive system. A need in the industry exists for a rotational shock tester that allows for the measurement of rotational shock tolerances, and further, allows for an evaluation of the disc drive system such that the disc drive system can be designed to minimize susceptibility to rotational shock.

SUMMARY OF THE DISCLOSURE

Embodiments of the instant invention are directed to a shock tester system that measures the amount of rotational force that a latch mechanism on a disc drive can withstand prior to uncoupling such that the actuator is dislodged from its parked position.

Embodiments of the rotational shock tester system comprise a disc drive support system, a drop mechanism and an impact apparatus. The disc drive support system includes a plurality of plates, wherein the plates include a mounting plate, a rotation plate and a center of gravity plate. The plates are coupled together such that the rotation plate and center of gravity plates are free to rotate in relation to the mounting plate. The disc drive to be tested is mounted to the center of gravity plate.

The drop mechanism, which is coupled to the disc drive support system, includes a plurality of blocks and an elevating apparatus, wherein the plurality of blocks include at least one elevating block, or drop block, and a stationary block, or a linear drop stopper, wherein the blocks are stacked on top of each other. The elevating apparatus is configured to elevate and release the drop block such that upon release the drop block will return to its position adjacent the linear drop stopper.

The impact apparatus is releasably coupled to the drop mechanism and is aligned with the plurality of plates such that upon release of the drop block, the rotation plate impacts the impact apparatus such that the impact apparatus imparts an angular acceleration to the rotation plate and imparts a rotational shock to the disc drive. The impact apparatus can be coupled to the drop mechanism such that the rotation plate rotates either clockwise or in a counter clockwise direction.

BRIEF DESCRIPTION OF THE DRAWINGS

The detailed description of embodiments of the invention will be made with reference to the accompanying drawings, wherein like numerals designate corresponding parts in the figures.

DETAILED DESCRIPTION OF EMBODIMENTS

Embodiments of the instant invention are directed to a shock tester system that measures the amount of rotational force that a latch mechanism on a disc drive can withstand prior to uncoupling such that the actuator is dislodged from its parked position. Embodiments of the shock tester system 10 comprise a drop mechanism 20, an impact apparatus 40 and a disc drive support system 80.

Figure 1:
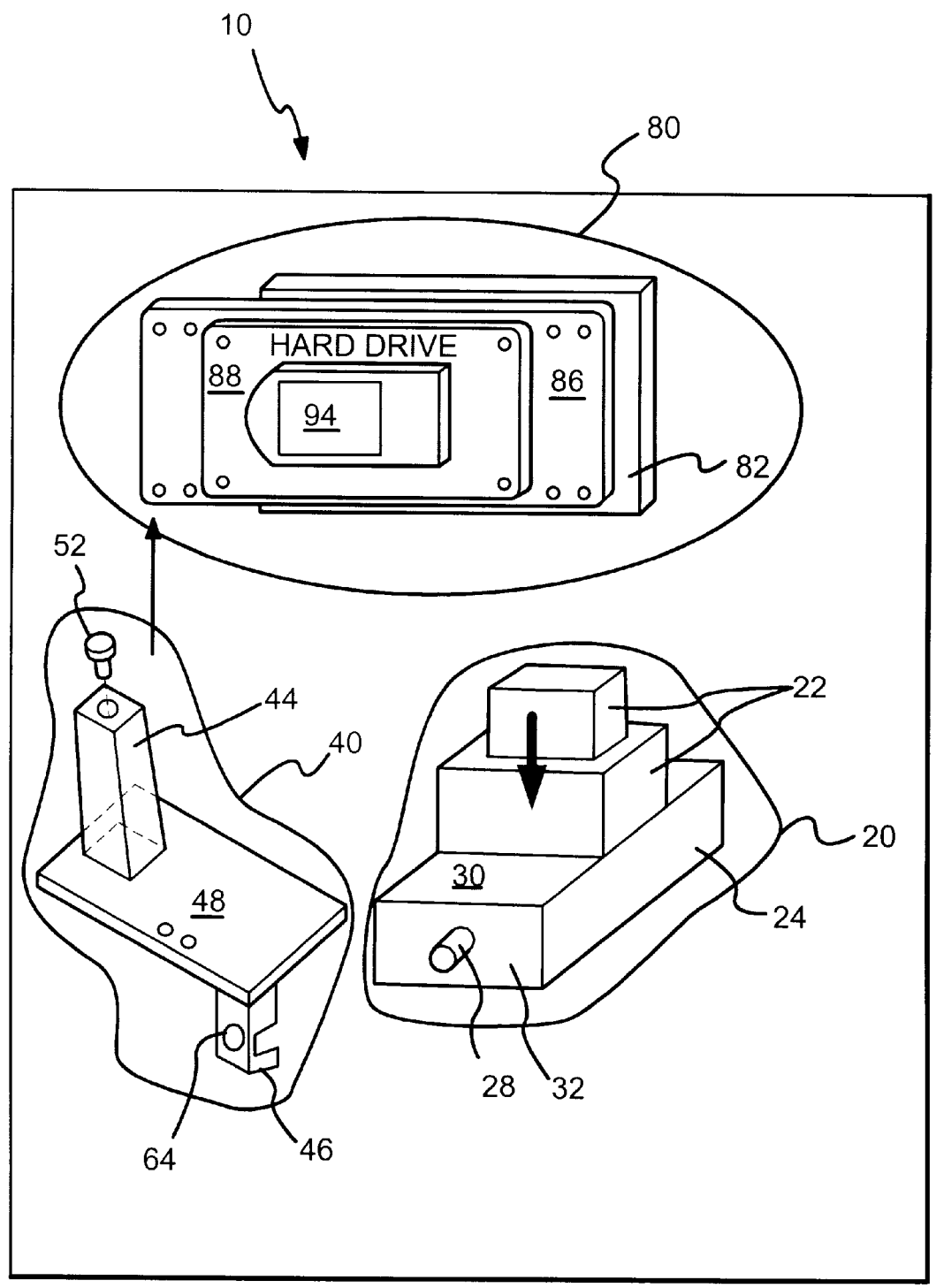
FIG. 1 depicts an exploded view of an embodiment of the rotational shock tester of the instant invention.

With reference to FIG. 1, the drop mechanism 20 is an apparatus comprising a plurality of drop blocks 22, a linear drop stopper 24, pulleys 26 (see FIG. 4), and a mounting pin 28. The drop blocks 22 are blocks that are made from magnesium, aluminum or stainless steel, although any material that is rigid enough to not crack or bend during dropping or impact is suitable. In embodiments, wherein one drop block 22 is used, materials such as aluminum or stainless steel increase the weight or mass of the system. In other embodiments, magnesium is chosen to increase damping of the impact. When multiple drop blocks 22 are used, the drop blocks 22 are bolted together, or are attached by any other suitable means that will prevent the drop blocks 22 from separating during the testing. In some embodiments, the drop blocks 22 are stacked, from top to bottom in ascending order of size.

The linear drop stopper 24 is a rectangular block having a top surface 30 and a coupling side 32. The top surface 30 supports the drop blocks 22 which are disposed on the linear drop stopper 24. The linear drop stopper 24 is preferably larger in size than the drop blocks 22 such that when the drop blocks 22 are stacked on the linear drop stopper 24, the blocks are arranged, from top to bottom, in increasing size. Although the linear drop stopper 24 is rectangular in shape, any shape that can support the drop blocks 22 is suitable. The linear drop stopper 24 is made from cast iron, or any other material that can provide a sturdy base.

A mounting pin 28 is coupled to the coupling side 32 of the linear drop stopper 24. The mounting pin 28 protrudes perpendicularly from the surface of the coupling side 32. The mounting pin 28 is cylindrical in shape, although any shape that is capable of coupling the drop mechanism 20 to the impact mechanism 40 (discussed below) is suitable. The mounting pin 28 is made from hard plastic, wood or any other material which is durable to sustain the coupling between the drop mechanism 20 and the impact mechanism 40. In preferred embodiments, the mounting pin 28 protrudes about 1.0 inches (2.54 cm) from the coupling side 32.

Figure 2:
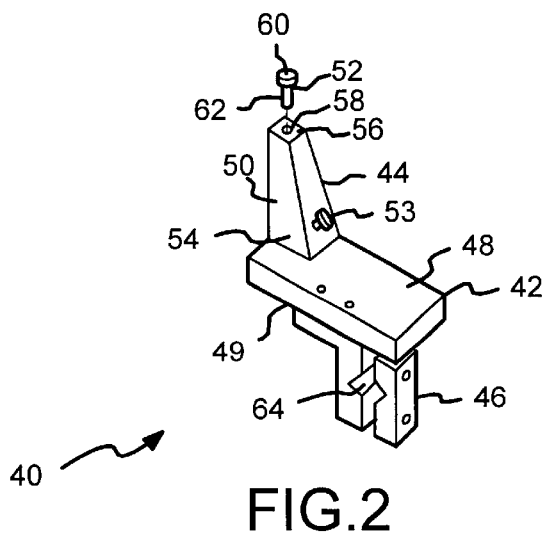
FIG. 2 depicts the embodiment of the impact mechanism of FIG. 1.

The impact mechanism 40 comprises a platform 42, an impact tower 44 and a mounting station 46. With reference to FIG. 2, the platform 42 is a horizontal member having a top surface 48 and a bottom surface 49. In some embodiments, the platform 42 is rectangular in shape, although other shapes, such as, a square or triangle are also suitable. The platform 42 is made from sturdy materials, including, but not limited to, plastics, wood and metal alloys.

The impact tower 44 is disposed on the top surface 48 of the platform 42. The impact tower 44 comprises an elongated body 50, an impact member 52 and a stop pin 53. The elongated body 50 includes a base 54 and top portion 56, wherein the top portion 56 includes an aperture 58. The elongated body 50 is rectangular in shape, wherein the base 54 of the rectangle is wider than the top portion 56. The base 54 of elongated body 50 is disposed on the top surface 48 of the platform 42 such that the top portion 56 is elevated above the platform top surface 48. In preferred embodiments, the elongated body 50 is about 6 inches (15.24 cm) in length such that when it is disposed on the top surface 48, the top portion 56 is about 6 inches (15.24 cm) above the top surface 48.

The stop pin 53 is coupled nearer in proximity to the base 54 of the elongated body 50 than the top portion 56. The stop pin 53 is made from aluminum, although any material capable of withstanding an impact between about 2000–3000 Newtons of force is suitable. In some embodiments, felt is added to the top portion 56 of the stop pin 53 so as to reduce the force of the impact.

The impact member 52 is a pin having a head 60 and a cylindrical member 62, wherein the head 60 is coupled to the cylindrical member 62. The impact member 52 can be made as a single piece or the head 60 and cylindrical member 62 can be separately manufactured and coupled together by any suitable means, including, gluing, welding or soldering. The cylindrical member 62 is received in the aperture 58 such that the head 60 resides adjacent the top portion 56.

The impact member 52 determines the drop height, or pulse rate, for the shock test. The drop height determines how much force is imparted to the disc drive 94. The more flexible, or softer, the material of the impact member 52, the larger the width of the pulse rate and the lower its amplitude. The stiffer, or harder, the material of the impact member 52, the smaller the width of the pulse rate and the higher the amplitude. A higher amplitude pulse rate, or a larger drop height, corresponds to a greater force being imparted to the disc drive 94. In preferred embodiments, shock pulses, or the intensity of the impact ranges from about 0.1 msec–11 msec, wherein the intensity is determined by the thickness of cushion, that is, the flexibility of the material, of the impact member 52. The impact member 52 is made from aluminum. However, to achieve a range of drop heights, the head 60 is covered with a variety of materials, including, but not limited to, rubber, felt and plastics (softer materials) and plastics and stainless steel (stiffer materials). In one preferred embodiment, the drop height is 0.3 m (11.8 inches), wherein a rotational shock of about 10,000 rad/s$^2$ can be achieved. In other embodiments, accelerations of up to about 50,000 rad/s$^2$ can be achieved by varying the drop height.

The mounting station 46 is disposed on the bottom surface 49 of the platform 42. The mounting station 46 includes a receiving aperture 64, wherein the receiving aperture 46 is configured to receive the mounting pin 28. When the mounting pin 28 is received in the receiving aperture 64, a portion of the bottom surface 49 of the platform 42 resides adjacent the top surface 30 of the linear drop stopper 24. The platform 42 extends onto the top surface 30 a sufficient amount such that the coupling between the impact apparatus 40 and the drop mechanism 20 is stable. Further, when the mounting pin 28 is received in the aperture 64, the coupling side 32 of the linear drop stopper 24 resides adjacent the mounting station 46. In one preferred embodiment, the coupling side 32 abuts the mounting station 46.

Figure 3A:
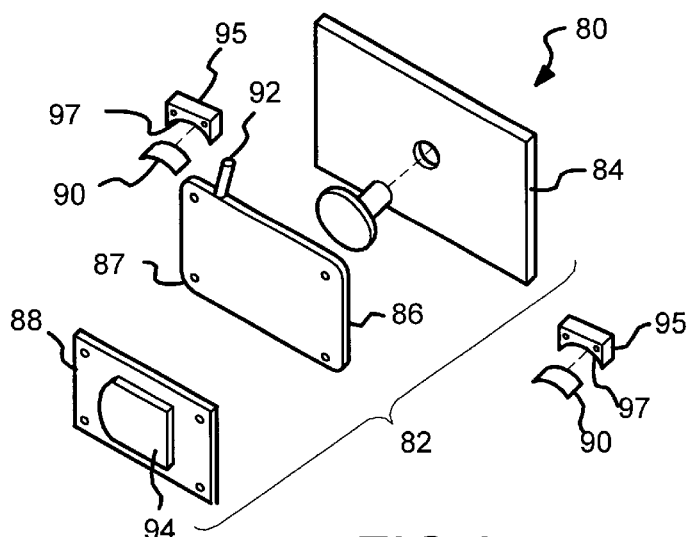
FIG. 3a depicts an exploded view of the disc support system of FIG. 1.
Figure 3B:
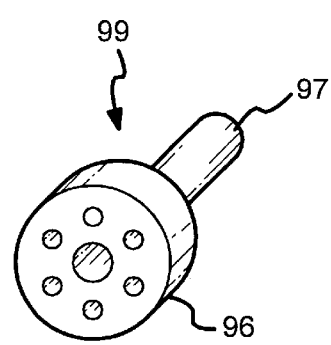
FIG. 3b depicts a coupling member for coupling the mounting plate to the rotation plate of FIG. 1.

With reference to FIG. 3, the disc drive support system 80 comprises a plurality of plates 82, including a mounting plate 84, a rotation plate 86 and a center of gravity plate 88. The plurality of plates 82 are made from materials, including, but not limited to, metals, metal alloys, and plastics. The plates 82 are rectangular in shape and are initially stacked together such that the elongated axis are aligned.

The mounting plate 84 includes friction pads 90 and friction pad holders 95, wherein the mounting plate 84 is coupled to the side of the bottom most drop block 22 by coupling member 91. Once coupled, the mounting plate 84 is flush against the top most drop block 22 and is disposed over the top surface 30 of the linear drop stopper 24. The drop blocks 22 are coupled to the linear drop stopper 24 via bolting, or are attached by any other suitable means that will prevent the drop blocks 22 and linear stopper 24 from separating during the testing.

The friction pad holders 95 are rectangular blocks wherein the rectangle included a curved surface 97. The friction pad holders 95 are mounted to the mounting plate 84. The friction pads 90 are coupled to the curved surface 97 and control the angular deceleration of the rotation plate 86. The pads 90 allow for a smooth deceleration and are designed to prevent a reverse pulse from being induced to stop the angular rotation of the rotation plate 86. If a reverse pulse is induced, the results of the test would be invalid because a shock pulse is generated in the opposite direction negating the effect of the initial pulse.

The rotation plate 86 includes an impact point 87. In one embodiment, the rotation plate 86 is about 0.21 m by 0.15 m. The rotation plate is coupled to the mounting plate 84 via a coupling member 99, which includes a ball bearing member 96 and a shaft 97, wherein the shaft 97 is coupled to the center of the ball bearing member 96 (see FIG. 3*b*). In one embodiment, the ball bearing member 96 is press fit into the back of the rotation plate 86. In other embodiments (not shown), the rotation plate 86 is coupled to the outer race of the ball bearing member 96 via a plate mounted onto the back of the rotation plate 86. The rotation plate 86 is coupled to the mounting plate 84 such that rotation plate 86 is capable of rotating or spinning. Once coupled, the impact point 87 of the rotation plate 86 extends beyond the edges mounting plate 84.

An accelerometer 92 is coupled to one corner of the rotation plate 86 such that the acceleration of the rotation plate 86 can be measured. In one embodiment, the accelerometer 92 is a linear accelerometer, wherein the measurements are converted into angular momentum using the radius of the rotation plate 86 to the accelerometer 92.

The center of gravity of plate 88 is coupled to the rotation plate 86. The center of gravity plate 88 is secured such that it does not move relative to the rotation plate 86, but rather, spins or rotates with the rotation plate 86. The elongated axis of the center of gravity plate 88 is shorter than the elongated axis of the rotation plate 86 such that the center of gravity plate 88 resides entirely on or within the boundary edges of the rotation plate 86. In some embodiments, the dimensions of the center of gravity plate are about 0.16–0.20 m by 0.11 m–0.14 m. In one embodiment, the center of gravity plate 88 is about 0.17 m by 0.13 m. As the loading conditions at different locations on the disc drive must be considered, any dimensions of the center of gravity plate 88 that are proportional to the dimensions of the rotation plate 86 are suitable. The disc drive 94 is attached to the center of gravity plate 88. In one preferred embodiment, the disc drive 94 is attached such that the center of rotation is through the actuator pivot of the disc drive 94.

The design of the disc drive support system 80 is dependent, in part, on the load conditions imposed on the bearings of the system. Calculation of the load conditions imposed by the rotation plate 86 and the center of gravity plate 88, in part, determine the magnitude of the angular acceleration experienced by the system upon impact, and thus, effect the size and thickness of these plates.

Figure 4:
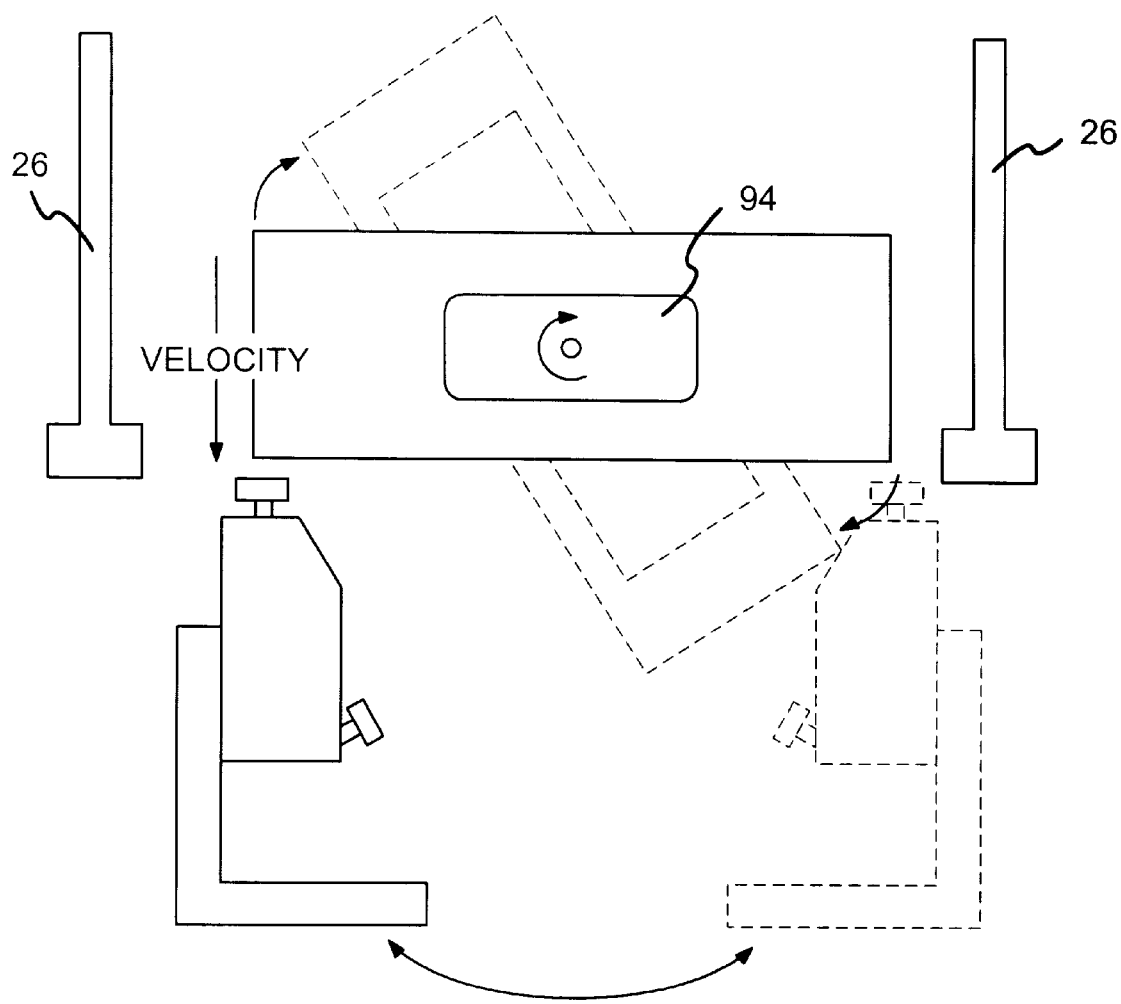
FIG. 4 depicts a side view of the embodiment of FIG. 1 in an assembled state.

FIG. 4 depicts a side view of an assembled rotational shock system, wherein the rotation of the plates is counter clockwise. As depicted in FIG. 4, the impact apparatus 40 is bi-directional, that is, it can be mounted such that the impact tower 44 is on either side of the linear drop stopper 24. Thus, the rotation of the plates can be either clockwise or counter clockwise.

Pulleys 26 are coupled to the drop blocks 22. The pulleys 26 are configured to elevate the drop blocks 22 above the linear drop stopper 24. Further, the pulleys 26 are configured such that they do not interfere with the disc drive supporting system 80. The configuration of the pulleys 26 are well known in the art.

Referring to FIG. 4, in operation, the disc drive 94 to be tested is secured to the center of gravity plate 88. The disc drive 94 is aligned with the plurality of plates 82 such that the elongated sides of the plates 82 and the disc drive 94 reside in parallel planes. The drop blocks 22, which are coupled to the plurality of plates 82, and thus, the disc 94, are raised by the pulleys 26 such that the drop blocks 22 separates from the linear drop stopper 24. In raising the drop blocks 22 the plurality of plates is also raised. The drop blocks 22 are then released and, due to gravity, descend downward towards the linear drop stopper 24. As the drop blocks 22 and plates 82 descend the impact point 87 of the rotation plate 86 collides against the impact member 52. The collision with the impact member 52 causes the rotational plate 86 to spin. In the embodiment illustrated in FIG. 4, the rotational plate 86 spins in the clockwise direction. The stiffness of the impact member 52 determines the amount of rotational force imparted to the disc drive 94.

During the spinning of the rotational plate 86 on the mounting plate 84, a corner of the rotation plate 86 passes over curved surface 97 of the friction pad holders 95 such that the plate 86 passes over the friction pad 90. Due to friction, the friction pad 90 slows, and stops, the rotation of the rotational plate 86. If the rotation of the rotational plate 86 is not stopped by the friction pads 90, the rotational plate 86 spins until it collides with the stop pin 53.

While the rotational plate 86 is spinning the drop blocks 22 are descending. A second impact is imparted to the disc drive 94 when the drop blocks 22 return to their original position on the top surface 30 of the linear drop stopper 24. Thus, two impacts are imparted to the disc drive 94 during this process. During a typical test, the plates 82, and thus, the disc drive 94 have ceased spinning prior to the second impact caused by the drop blocks 22 colliding with the top surface 30 of the linear drop stopper 24.

It is to be understood that even though numerous characteristics and advantages of various embodiments of the present invention have been set forth in the foregoing description, together with details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, the particular elements may vary depending on the particular application for the disc drive assembly while maintaining substantially the same functionality without department from the scope and spirit of the present invention. For instance, in one embodiment, a high speed camera is integrated into the rotational shock tester system such that the effects of the collision on the latch can be reviewed, thus, allowing evaluation of the latch design. It will be appreciated by those skilled in the art that the teachings of the present invention can be applied to other systems without departing from the scope and spirit of the present invention.

What is claimed is:

1. An apparatus for imparting a rotational shock to a disc drive, comprising:

a disc drive support system having a plurality of plates, wherein a disc drive is mounted to a rotation plate, which is a rotatable one of the plurality of plates;

a drop mechanism having a plurality of blocks, including an elevating block and a stationary block, and an elevating apparatus, wherein the drop mechanism is coupled to the disc drive support system; and wherein the elevating apparatus is configured to elevate and release the elevating block such that upon release the elevating block will return to its position in relation to the stationary block; and an impact apparatus, wherein the impact apparatus is configured to releasably couple to the drop mechanism, and wherein the impact apparatus is aligned with the plurality of plates such that upon release of the elevating block, the rotation plate impacts the impact apparatus, wherein the impact apparatus imparts an angular acceleration to the rotation plate and imparts a rotational shock to the disc drive.

2. An apparatus as claimed in claim 1, wherein the impact apparatus further comprises:

a platform having a top surface and a bottom surface;

an impact tower; and a mounting station, wherein the impact tower is disposed on the top surface and the mounting station is disposed on the bottom surface.

3. An apparatus as claimed in claim 2, wherein the impact tower further comprises:

a body having a first end and a second end;

an impact member disposed nearer the first end of the body; and a stop pin, wherein the stop pin is disposed nearer the second end of the body.

4. An apparatus as claimed in claim 3, wherein upon release of the elevating block the rotation plate impacts the impact point.

5. An apparatus as claimed in claim 1, wherein the plurality of plates comprise:

a mounting plate;

a rotation plate, wherein the rotation plate is coupled to the mounting plate such that it is configured to rotate; and a center of gravity plate, wherein the center of gravity plate is coupled to the rotation plate such that it rotates in conjunction with the rotation plate; and wherein the disc drive is coupled to the center of gravity plate.

6. An apparatus for imparting a rotational shock to a disc drive, comprising:

a disc drive support system for supporting a disc drive, wherein disc drive is rotatably mounted to the disc drive support system;

a disc drive dropping means having an elevating apparatus for elevating the disc drive support system, wherein the disc drive dropping means is coupled to the disc drive support system; and wherein the elevating apparatus is configured to elevate and release the disc drive support system; and an impact means for imparting a rotational shock to the disc drive, wherein the impact means is configured to releasably couple to the disc drive dropping means, and wherein the impact means is aligned with the disc drive support system such that upon release of the disc drive support system, the disc drive support system impacts the impact means and imparts a rotational shock to the disc drive.

* * * * *